United States Patent [19]

Abdullah et al.

[11] 4,226,937

[45] Oct. 7, 1980

[54] METHOD USING GLUCOAMYLASE IMMOBILIZED ON POROUS ALUMINA

[75] Inventors: Mukhtar Abdullah, Downers Grove; Frederick C. Armbruster, LaGrange, both of Ill.

[73] Assignee: CPC International Inc., Englewood Cliffs, N.J.

[21] Appl. No.: 33,913

[22] Filed: Apr. 27, 1979

[51] Int. Cl.$^2$ .............................................. C12P 19/20
[52] U.S. Cl. .................................................. 435/96
[58] Field of Search ................... 435/96; 127/40, 46 A

[56] References Cited

U.S. PATENT DOCUMENTS

| | | |
|---|---|---|
| 4,011,137 | 3/1977 | Thompson et al. .................. 435/96 |
| 4,132,595 | 1/1979 | Hebeda et al. ....................... 435/96 |

*Primary Examiner*—Lionel M. Shapiro
*Attorney, Agent, or Firm*—Stanley M. Parmerter

[57] ABSTRACT

A process for the production of dextrose-containing syrups wherein a deionized starch hydrolyzate is treated with glucoamylase immobilized on porous alumina.

7 Claims, No Drawings

METHOD USING GLUCOAMYLASE IMMOBILIZED ON POROUS ALUMINA

FIELD OF INVENTION

This invention relates to the production of dextrose and dextrose-containing syrups through the use of an immobilized glucoamylase enzyme.

BACKGROUND OF INVENTION

Starch is a polymeric carbohydrate of very high molecular weight. Its monomeric units, termed anhydroglucose units, are derived from dextrose, and the complete hydrolysis of starch yields dextrose. In the United States, dextrose is manufactured from corn starch; in Europe from corn starch and potato starch; and in Japan from corn starch and white sweet potato starch.

Until 1960, dextrose was prepared from starch by acid hydrolysis. The method of preparation involved heating starch with hydrochloric or sulfuric acid at temperatures of 120°–145° C., then neutralizing the hydrolysis mixture with sodium carbonate, clarifying, and crystallizing the dextrose. Unfortunately, the yield of dextrose is lowered by the formation of relatively large amounts of reversion products, i.e., products which are formed by the recombination of dextrose molecules. Also, because of the high temperature and low pH of the hydrolysis reaction, some of the dextrose produced is converted to hydroxymethylfurfural, levulinic acid and color bodies. The formation of such degradation products is irreversible and, to the extent they are formed, the yield of desired dextrose is, of course, adversely affected. Still further, the use of hydrochloric acid or in some instances, sulfuric acid, and the subsequent neutralization of this acid with alkali results in the formation of inorganic salts which interfere with crystallization of the final dextrose product.

Later, hydrolysis of starch to dextrose was accomplished by means of enzymes. The principal enzyme used for this purpose was, and continues to be, glucoamylase. This enzyme effectively hydrolyzes the starch by cleaving one molecule of dextrose at a time from the starch molecule. As a practical matter, however, it is necessary first to reduce the molecular weight of the starch by partial hydrolysis before subjecting it to the action of glucoamylase. This process, called thinning, may be accomplished either by means of acid or enzyme. The starch is thinned to a dextrose equivalent (D.E.) of about 10–20, then treated with glucoamylase. This two-stage process is referred to as an acid-enzyme process or an enzyme-enzyme process, depending upon the nature of the thinning step employed.

In the acid-enzyme process, starch is liquefied and hydrolyzed in an aqueous suspension containing 20 to 40 percent starch and an acid, such as hydrochloric acid. The suspension is then heated to a high temperature, i.e., a temperature between about 70° C. and about 160° C. and at a pH between about 1 and 4.5 to liquefy and partially hydrolyze the starch. Typical acid-enzyme processes are disclosed in U.S. Pat. Nos. 2,305,168; 2,531,999; 2,893,921; 3,021,944 and 3,042,584.

In the enzyme-enzyme process, starch is liquefied and partially hydrolyzed in an aqueous suspension containing 20 to 40 percent starch and a liquefying enzyme, such as bacterial α-amylase enzyme at a temperature of from about 85° C. to about 105° C. The dextrose equivalent of the liquefied and partially hydrolyzed starch is generally less than about 20 and preferably less than about 10. The mixture is then subjected to a temperature above about 95° C. and preferably between 110° C. and 150° C. to insure complete starch solution. The starch hydrolyzate is then cooled to a temperature of less than 95° C. and subjected to further treatment with bacterial α-amylase to hydrolyze the starch to a D.E. of about 10 to 20. This process is disclosed and claimed in U.S. Pat. No. 3,853,706.

By either process the thinned starch may thereafter be converted to dextrose or dextrose-containing syrups by other enzymes such as glucoamylase. Glucoamylase preparations are produced from certain fungi strains such as those of the genus Aspergillus; for example, Aspergillus phoenicis, Aspergillus niger, Aspergillus awamori, and certain strains from the Rhizopus species and certain Endomyces species. Glucoamylase effects the hydrolysis of starch proceeding from the non-reducing end of the starch molecule to split off single glucose units at the alpha-1,4 linkages or at the alpha-1,6 branch points. Commercial glucoamylase enzyme preparations comprise several enzymes in addition to the predominating glucoamylase; for example, small amounts of proteases, cellulases, α-amylases, and transglucosidases.

Considerable interest has developed in the use of immobilized enzyme technology for the production of dextrose or dextrose-containing syrups from starch. In this technology, the enzyme, attached to some insoluble support material, may be reused repeatedly, and a more precise control of the reaction is possible. Various procedures have been described for the immobilization of glucoamylase. These include covalently binding an enzyme to an insoluble carrier, adsorption of an enzyme on an insoluble carrier followed by cross-linking of the enzyme to prevent an escape from the carrier, and entrapment of the enzyme within the pores of a porous material. References which review the art of enzyme immobilization, with particular attention to the immobilization of glucoamylase, are given in U.S. Pat. No. 4,011,137.

Several reports have been made of attempts to immobilize glucoamylase on alumina. Usami and Taketomi, Hakko Kyokaiski, 23, 267–9 (1965), reported that various substances including alumina could adsorb "Glucoteem" from solution. However, there was no mention of any further use of the adsorbed material. Solomon and Levin, Biotechnol. Bioeng., 17, 1323–1333 (1975), reported that amyloglucosidase was adsorbed on 4 of the 7 samples of activated alumina they tested. Inactivation of the enzyme composite was observed when it was exposed to a starch hydrolyzate, and the amount of inactivation increased as the substrate concentration increased. When the alumina was treated with a dye prior to adsorption of the enzyme and the mixture was further reacted with glutaraldehyde, the useful life of the immobilized enzyme was increased.

In U.S. Pat. No. 3,850,751, it was disclosed that various enzymes are adsorbed on alumina, titania and zirconia of specified pore size. There was no mention of the binding of glucoamylase to these inorganic supports.

The reported uses of alumina or other inorganic carriers as supports for immobilizing glucoamylase generally requires chemical reaction to cross link the enzyme and/or to attach the enzyme to the carrier. Such chemical treatment destroys much of the enzyme activity and increases the cost of the process. The processes usually operate at temperatures of 50° C. or below. At these temperatures bacterial contamination is frequently a problem, and conversion of the starch hydrolyzate to dextrose is slow. Furthermore, when these enzyme composites are used in plug-flow reactors, the hydrolyzate must be treated at such a slow flow rate that the process is not practical for commercial use.

SUMMARY OF THE INVENTION

We have discovered a process which does not require a chemical reaction to immobilize the glucoamylase on the support. The immobilized glucoamylase, when used in this process, shows a long useful life at temperatures of 60° C. and is not eluted from the carrier. Furthermore, a starch hydrolyzate may be passed through the immobilized enzyme in a plug-flow reactor at a practical rate of flow. According to this process, the glucoamylase is first adsorbed on porous alumina. The resulting enzyme composite is then contacted with a starch hydrolyzate which has been treated with ion-exchange resin until it contains less than 0.1% ash on a dry basis. The treated hydrolyzate is separated from the enzyme composite, and the dextrose product is recovered from the treated hydrolyzate.

DESCRIPTION OF PREFERRED EMBODIMENTS

Any alumina may be used in this process which will bind the glucoamylase. Preferably the alumina will have a high surface area and be water insoluble. It must have a pore diameter such that the enzyme is adsorbed on the surface in an active form and yet will not be leached from the carrier on passage of aqueous solutions over the immobilized enzyme composite. Preferred aluminas are those which have an average pore diameter of 200–1000 Å, more preferably 300–700 Å. The mesh size of the alumina will vary with the application to be used. A convenient mesh size for use in a plug-flow column is a 30/45 mesh. The preferred alumina has a surface area in the range of 20–100 m²/g of alumina. It may contain up to 10% magnesium oxide but a preferred alumina is one that is essentially free of magnesium. Suitable aluminas produced by the Corning Glass Works, Corning, N.Y., are described in U.S. Pat. Nos. 3,850,751, 3,868,304 and 3,992,329. Other aluminas with similar properties may be used.

The glucoamylase used in this invention may be any of the well-known fungal amylase preparations, particularly those derived from members of the Aspergillus genus, the Endomyces genus or the Rhizopus genus. A particularly preferred glucoamylase is that available from the process described in U.S. Pat. No. 3,042,584 (Kooi, et al) whereby a fungal amylase preparation is freed of undesired transglucosidase activity by treatment in an aqueous medium with a clay material. The enzyme may be further purified by precipitation from an aqueous solution with an organic solvent, such as acetone.

Glucoamylase activity units are determined as follows:

The substrate is a 10-20 D.E. alpha-amylase thinned hydrolyzate of waxy maize starch dissolved in water and diluted to 4.0 grams of dry substance per 100 ml of solution. Exactly 50 ml of the solution is pipetted into a 100 ml volumetric flask. To the flask is added 5.0 ml of 1.0 molar sodium acetate-acetic acid buffer (pH 4.3). The flask is placed in a water bath at 60° C. and after 10 minutes the proper amount of enzyme preparation is added. At exactly 120 minutes after addition of the enzyme preparation, the solution is adjusted to a phenolphthalein end point with 0.5 N sodium hydroxide. The solution is then cooled to room temperature and diluted to volume. A reducing sugar value, calculated as dextrose, is determined on the diluted sample and on a control with no enzyme preparation added. Glucoamylase activity is calculated as follows:

$$A = \frac{S - B}{2 \times E}$$

where:
 A = Glucoamylase activity units per ml (or per gram) of enzyme preparation.
 S = Reducing sugars in enzyme converted sample, grams per 100 ml.
 B = Reducing sugars in control, grams per 100 ml.
 E = Amount of enzyme preparation used, ml (or grams).
 S should not exceed 1.0 gram per 100 ml.

The half-life of soluble glucoamylase was determined by allowing a solution containing 30 units of the enzyme in 400 grams of a 25% solution of an ion-exchanged 29 D.E. alpha-amylase thinned starch hydrolyzate to react at 60° C. and pH 4.3 for 4 days. The volume and pH levels were adjusted daily to maintain their original values. Residual glucoamylase activity was determined after 4 days' reaction. Half-life was determined graphically by plotting the log of the percentage of remaining activity versus time. Half-life was defined as the time required to attain half the initial enzyme activity.

Half-life of the immobilized glucoamylase was determined in a similar manner to that used for the soluble glucoamylase except that approximately 2 grams of the enzyme conjugate was used with 400 grams of the hydrolyzate solution. After 7 days of reaction, the enzyme composite was recovered quantitatively by vacuum filtration, washed with about 200 ml of distilled water and enzyme activity determined on the residual solid. The half-life was calculated from the percent of remaining activity in the same manner as for soluble glucoamylase. Half-life for the enzyme conjugate determined in this batchwise manner was essentially the same as that determined from column operation.

The glucoamylase to be contacted with the alumina is used in solution after proper dilution with water. Dilution may also be made with a solution of a salt that stabilizes the enzyme or with a solution of a buffer which maintains the pH. The preferred concentrations are 5 to 200 units of enzyme per milliliter.

Adsorption of the enzyme on the carrier is a single-step reaction and no coupling or cross-linking agent is employed. The alumina is preconditioned by shaking it with 5 to 10 times its weight of a dilute buffer solution at a pH of about 4 to 6. The buffer is decanted and a solution of the glucoamylase in a fresh buffer is then contacted with the alumina generally at or below room temperature for a time sufficient to cause adsorption of the enzyme. Adsorption of the enzyme may be accomplished by stirring or shaking a solution of the enzyme with the alumina or by other means of maintaining the contact until adsorption is complete. Any excess enzyme is removed and the enzyme alumina conjugate is then rinsed with water and buffer.

The starch hydrolyzate used as starting material may be prepared by the liquefaction and hydrolysis of an aqueous suspension of starch using an acid, an enzyme or a combination of acids and enzymes as previously described. The D.E. of the starting starch hydrolyzates used in the practice of this invention may vary over a wide range but they preferably will be in the D.E. range of between about 10 and 80.

The term dextrose equivalent or D.E. value used herein refers to the reducing sugars content of the dissolved solids in a starch hydrolyzate expressed as percent dextrose as measured by the Schoorl method (Encyclopedia of Industrial Chemical Analysis, Vol. 11, pp 41–42).

The pH of the substrate may vary from 3.5 to 7.0 with the optimum pH varying with the enzyme used. With the glucoamylase preparation obtained from the fungal amylases of the Aspergillus genus, the pH of the starch hydrolyzate is maintained between about 3.5 and 5.5 with the preferable pH range being between about 4.2 and 4.5.

It has been found that the presence of inorganic salts in the starch hydrolyzate used in the preparation of dextrose-containing syrups by this invention has a marked influence on the ability of the alumina to retain the sorbed glucoamylase. Starch hydrolyzate which analyzes for 0.5% ash causes a steady elution of the enzyme from the alumina carrier. However, an ion-exchanged starch hydrolyzate containing less than 0.1% ash, preferably less than 0.05% ash, causes no appreciable elution of the glucoamylase from the alumina.

Hydrolyzate ash is determined by weighing a 5-gram sample (dry basis) in an accurately weighed 100-ml evaporating dish. The material is evaporated to dryness on a hot plate before it is placed in a muffle furnace. It is heated at 550° C. for 2 hours or until free from carbon. The dish is cooled in a desiccator and weighed.

$$\text{Ash \%} = \frac{\text{Residue Weight} \times 100}{\text{Sample Weight (dry basis)}}$$

A wide range of concentrations of the starting starch hydrolyzates may be used in the practice of this invention. They may range in concentration from 5 to 60% solids; however, substrates with low D.E. may be too viscous for use at the higher solids concentrations.

The immobilized enzyme composite of this invention is contacted with a starch hydrolyzate at such a temperature as to give a practical rate of reaction without causing an impractical loss of enzyme activity. The useful temperature range is 20° C. to 70° C. and the preferred range is from about 50° C. to about 60° C.

The immobilized enzyme composite of this invention may be contacted with a starch hydrolyzate in any of the conventional ways. One method is to place the enzyme composite in a column and pass the starch hydrolyzate through the insoluble enzyme composite in either a downflow or upflow manner. Likewise, a batch method may be used whereby the immobilized enzyme composite is contacted with a starch hydrolyzate in a reaction vessel. At the completion of the reaction, the immobilized enzyme composite may be removed from the starch hydrolyzate by filtration or decantation. Other methods will be obvious to those skilled in the art.

The enzyme composite may be separated from the immobilized enzyme composite at the end of the reaction by any conventional means. If the starch hydrolyzate is passed through a column containing immobilized enzyme composite, the product is automatically separated from the enzyme as it leaves the column. In batch processes, the enzyme composite is separated from the hydrolyzate by such means as filtration, centrifugation or decantation.

Dextrose syrups obtained by this process were analyzed using high-performance liquid chromatography (HPLC). Components were chromatographed by elution with water from a cation-exchange resin in the calcium form. The general procedure is that given in "Analysis of Carbohydrate Mixtures by Liquid Chromatography," Am. Soc. Brew. Chem. Proc., 1973, pp 43–46. The resin used was Aminex Q 15S in the calcium form, Bio-Rad. Laboratories, Richmond, Calif. Eluted components were detected by means of a differential refractometer, plotted on a recorder and quantitated using an electronic integrator. The area under the curve which represents the concentration of each component is reported as a percentage of the total area. Values for oligosaccharides were expressed as DP2 for disaccharides, and DP3+ for trisaccharides plus higher oligosaccharides.

The dextrose-containing syrups obtained by the process of this invention may be further treated to convert them to products suitable for use as sweeteners or for use as intermediates in the production of other products. Such means may include evaporation, crystallization, separation or purification using resins or carbon. The amount of dextrose in the product may be varied by varying the contact time between the hydrolyzate and the enzyme, the temperature, the concentration of the hydrolyzate used and the composition of the hydrolyzate used. It is possible to produce syrups with controlled amounts of dextrose as well as those with high amounts of dextrose.

The invention is further illustrated by reference to the following examples in which all parts and percentages are by weight unless otherwise noted.

EXAMPLE 1

To 110 grams of porous alumina with an average pore diameter of 236 Å containing about 1.3% magnesium (as described in U.S. Pat. No. 3,992,329) was added 250 ml of 0.1 M acetate buffer, pH 5.0. The mixture was gently shaken using an orbital shaker for 1 hour at room temperature and the pH was controlled at 5.0 by periodic addition of 0.1 N acetic acid. The carrier was collected on a filter, washed with buffer and then shaken gently with 350 ml of a glucoamylase solution containing 17,600 units of glucoamylase dissolved in 0.1 M acetate buffer, pH 5.0. Gentle shaking was continued for 21 hours at room temperature before the conjugate was collected on a filter and washed with about 2 liters of distilled water. To a glass column (inside diameter 30 mm, length 190 mm) was added 100 ml of the enzyme/alumina conjugate. A 25% aqueous solution of an ion-exchanged, 29 D.E., alpha-amylase thinned, starch hydrolyzate (0.03% ash dry basis) was passed through the column at a rate of 1.0 to 3.5 B.V.H. for 7 days at 45° C. The pH of the feed was 4.3. It contained 0.025% propyl parasept to retard microbial growth. Effluent dextrose values as determined by HPLC averaged 92.3±0.2% over a flow range of 2.0–3.5 B.V.H. There was no detectable enzyme elution as determined by an assay for glucoamylase activity in the effluent. After 7 days of operation at 45° C., the glucoamylase/alumina conjugate was recovered. It showed no loss in glucoamylase activity indicating that the conjugate had a long half-life at this temperature.

EXAMPLE 2

A 20 ml portion of the enzyme conjugate used in the column operation in Example 1 was used in a smaller column for 9 days at 55° C. using the same feed liquor as in Example 1. Effluent dextrose level was constant at 91.0±0.1% over the flow range of 4.5–6.7 B.V.H. Assay of the enzyme conjugate after a total of 10 days in column operation at 55° C. showed a 14% loss in enzyme activity. This represents a projected half-life of 45 days for the enzyme conjugate under these operating conditions.

EXAMPLE 3

Twenty milliliters of the enzyme conjugate, prepared as described in Example 1, was placed in a column. A starch hydrolyzate as used in Example 1 was passed through the column for 4 days at 60° C. at a flow rate of 2.4–4.0 B.V.H. The dextrose content, as determined by HPLC, averaged 91.0±0.5%. There was no active enzyme detectable in the column effluent. From an assay of the enzyme conjugate after 4 days of operation at 60° C., a projected half-life of 9 days for the enzyme conjugate was calculated.

EXAMPLE 4

The procedure of Example 2 was repeated using a 25% aqueous solution of an 11 D.E. alpha-amylase thinned starch hydrolyzate at a flow rate of 1.6–5.6 B.V.H. for 4 days. The maximum dextrose level attained was 86.9% at a flow rate of 3.5 B.V.H. The feed liquor, which had not been ion exchanged, contained 0.5% ash. During column operation, assay of the effluent showed that glucoamylase was leaching from the column in an active form. A meaningful half-life of the enzyme conjugate could not be determined because of enzyme loss due to leaching. Similar difficulties were observed in all experiments in which the feed liquor to the enzyme column had not been ion exchanged prior to use.

EXAMPLE 5

A sample of porous alumina essentially magnesium free, described in U.S. Pat. No. 3,850,751, with an average pore diameter of 275 Å was mixed with glucoamylase solution as described in Example 1. This enzyme composite showed a half-life of 11 days at 60° C. The enzyme composite prepared in Example 1 gave a half-life of 7.3 days when tested under the same conditions. The half-life of soluble glucoamylase under the same conditions is 4.1 days.

These results indicate that the sorbed enzyme composite is more stable than the free enzyme. They also indicate that the magnesium-free alumina gives a more stable enzyme composite than does alumina which contains magnesium.

EXAMPLE 6

Enzyme composites were prepared according to the method of Example 1 using glucoamylase and three different samples of magnesium-free porous alumina having average pore diameters of 275 Å, 450 Å, and 1095 Å, respectively.

Each enzyme conjugate was used to hydrolyze 29 D.E. starch hydrolyzates in a batch conversion according to the following procedure. A volume of the conjugate having 40 units of glucoamylase activity was quantitatively transferred to 400 grams of a 25% solution of an ion-exchanged, 29 D.E., alpha-amylase thinned, starch hydrolyzate which had been previously adjusted to 60° C. and pH 4.3. The mixture was stirred for 45 hours at 60° C. with the volume and pH being maintained at the starting levels. Periodically, 10 ml aliquots of the hydrolyzate were withdrawn, treated in a boiling water bath for 15 minutes and then analyzed by HPLC for dextrose, DP2 and DP3+. Results are given in Table I.

TABLE I
PROPERTIES OF GLUCOAMYLASE (GA) ADSORBED ON ALUMINA OF VARIOUS PORE DIAMETERS

| Average Pore Diameter (Å) | 275 | 450 | 1095 |
| --- | --- | --- | --- |
| Activity (U/g of Alumina) | | | |
| Enzyme Offered | 160 | 160 | 160 |
| Enzyme Bound | 156 | 142 | 55 |
| Half-Life (days) | | | |
| Immobilized GA | 11 | 15 | 5 |
| Maximum Dextrose (%) | | | |
| Immobilized GA | 92.4 | 92.3 | 93.3 |
| Approximate Time (hrs) to | | | |
| Form Maximum Dextrose | 30 | 20 | 35 |

These results show that samples of alumina having widely varying average pore diameters may be used to form enzyme composites with glucoamylase. The alumina with the average pore diameter of 450 Å gives an enzyme composite with a superior half-life to those formed with aluminas of 275 Å and 1095 Å average pore diameters. Under similar conditions soluble glucoamylase has a half-life of 4.1 days and gives 96.5% maximum dextrose.

We claim:
1. A process for converting a starch hydrolyzate to a dextrose-containing syrup which comprises:
    a. treating the starch hydrolyzate with ion-exchange resin until its ash content is less than 0.1% on a dry basis;
    b. contacting the deionized starch hydrolyzate with an immobilized enzyme composite consisting essentially of glucoamylase sorbed on porous alumina;
    c. separating the treated hydrolyzate from said enzyme composite; and
    d. recovering the dextrose product from the treated hydrolyzate.
2. The process of claim 1 wherein the pH of the starch hydrolyzate is maintained between about 3.5 and 5.5.
3. The process of claim 1 when the pH of the starch hydrolyzate is maintained preferably between about 4.2 and 4.5.
4. The process of claim 1 wherein the starch hydrolyzate has a D.E. of between about 10 and 80.
5. The process of claim 1 when the glucoamylase has been purified by precipitation with an organic solvent.
6. The process of claim 1 wherein the alumina is substantially magnesium free.
7. The process of claim 1 wherein the starch hydrolyzate is treated with the enzyme composite at a temperature of from about 50° C. to about 60° C.

* * * * *